United States Patent
Day et al.

(10) Patent No.: US 11,578,205 B2
(45) Date of Patent: Feb. 14, 2023

(54) ANTIMICROBIAL, NON-THROMBOGENIC POLYMER COMPOSITION

(71) Applicant: Lubrizol Advanced Materials, Inc., Cleveland, OH (US)

(72) Inventors: Roger W. Day, Solon, OH (US); Hua Zhang, Cottonwood Hts., UT (US); Richard Woofter, Medina, OH (US); Umit G. Makal, Kocaeli (TR); Kiara L. Smith, Mayfield Hts., OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 505 days.

(21) Appl. No.: 16/481,314

(22) PCT Filed: Jan. 30, 2018

(86) PCT No.: PCT/US2018/015841
§ 371 (c)(1),
(2) Date: Jul. 26, 2019

(87) PCT Pub. No.: WO2018/140911
PCT Pub. Date: Aug. 2, 2018

(65) Prior Publication Data
US 2021/0277231 A1 Sep. 9, 2021

Related U.S. Application Data

(60) Provisional application No. 62/451,903, filed on Jan. 30, 2017.

(51) Int. Cl.
| | |
|---|---|
| *C08L 75/08* | (2006.01) |
| *C08G 18/32* | (2006.01) |
| *C08G 18/76* | (2006.01) |
| *C08K 5/31* | (2006.01) |
| *A61L 101/32* | (2006.01) |
| *A61L 2/18* | (2006.01) |

(52) U.S. Cl.
CPC .................. *C08L 75/08* (2013.01); *A61L 2/18* (2013.01); *C08G 18/3206* (2013.01); *C08G 18/7657* (2013.01); *C08K 5/31* (2013.01); *A61L 2101/32* (2020.08); *A61L 2202/24* (2013.01); *C08G 2150/00* (2013.01)

(58) Field of Classification Search
CPC .......... C08L 75/08; C08L 33/14; C08L 33/16; C08K 5/31
See application file for complete search history.

(56) References Cited

U.S. PATENT DOCUMENTS

| | | | | |
|---|---|---|---|---|
| 7,771,743 B1 * | 8/2010 | Luthra | ................... | A61L 29/16 424/407 |
| 2011/0124772 A1 * | 5/2011 | Wang | ..................... | A01N 33/12 523/177 |
| 2012/0259064 A1 | 10/2012 | Greiner et al. | | |

FOREIGN PATENT DOCUMENTS

| | | |
|---|---|---|
| CN | 106146776 A | 11/2016 |
| EP | 0379269 A2 | 7/1990 |
| JP | 59-228856 A | 12/1984 |
| JP | 08-157641 A | 6/1996 |
| WO | 2009/148880 A2 | 12/2009 |
| WO | 2014/099923 A1 | 6/2014 |
| WO | 2016/018956 A1 | 2/2016 |
| WO | 2016/054320 A1 | 4/2016 |
| WO | 2016/172460 A1 | 10/2016 |

OTHER PUBLICATIONS

Silastic Silicone Information. Avient Distribution. https://now.avient.com/Dow_Corning_Corporation-Silastic_Q74765-PDQ74765MED907G60?cclcl=en_US. As viewed on Feb. 7, 2022. (Year: 2022).*

* cited by examiner

*Primary Examiner* — Stephen E Rieth
(74) *Attorney, Agent, or Firm* — Eryn Ace Fuhrer; Michael A. Miller

(57) ABSTRACT

The disclosed technology provides thermoplastic polyurethane compositions having antimicrobial properties while still maintaining good physical properties and good non-fouling properties, methods of making the same, and articles, including medical devices, made from such compositions. The disclosed technology includes a process of making an antimicrobial polymer composition, where the process includes mixing an antimicrobial additive into a base polymer and further includes mixing in a non-fouling additive, where the antimicrobial additive is chemically held in the composition and the antimicrobial and non-fouling additives do not negatively impact each other's effectiveness.

3 Claims, No Drawings

ANTIMICROBIAL, NON-THROMBOGENIC POLYMER COMPOSITION

CROSS REFERENCE TO RELATED APPLICATION

This application is a national phase entry under 35 U.S.C. 371 of PCT/US2018/015841 filed Jan. 30, 2018, which claims the benefit of U.S. Provisional Application No. 62/451,903 filed Jan. 30, 2017.

FIELD OF THE INVENTION

The disclosed technology provides thermoplastic polyurethane (TPU) compositions having antimicrobial properties while still maintaining good physical properties and good non-thrombogenic properties, methods of making the same, and articles made from such compositions.

BACKGROUND

Antimicrobials are chemical compounds that reduce and/or mitigate the growth or development of microbial organisms. Antimicrobial additives work by a variety of mechanisms dependent upon the mode of action, composition, degree of activity, and application. When used properly, antimicrobial compounds lead to the death or arrested growth of the targeted microorganisms. Since their discovery in the early 1900s, antimicrobials have transformed the prevention and treatment of infectious diseases. Antimicrobial additives are currently used across a very wide array of applications, including the use of antimicrobials in the polymeric materials used in various medical applications. For example, polymeric materials that include antimicrobial additives can be used to make articles and devices for medical applications that will then eliminate, reduce and/or mitigate the growth or development of microbial organisms and so assist in the prevention and treatment of infectious diseases.

However, antimicrobials may also be hazardous to human health. Therefore, there is a need for antimicrobial additives that do not derive their activity from eluting out of the materials in which they are use. Rather there is a need for antimicrobial additives which do not elute out of the materials in which they are used and which remain effective over the life of usage of the material, or the article or device made from the material in which the antimicrobial additive is used. Specifically, materials which provide significant antimicrobial effectiveness in various antimicrobial assays, which are also non-thrombogenic in the blood loop assay and which are non-eluding based giving a zero zone of inhibition in the standard zone of inhibition test method (AATCC 147 test protocol) are desired by the medical device industry to reduce the occurrence of biomaterial associated infections. If such properties can be obtained without the need for additional coating steps which add costs and additionally additional processing steps and which have been shown to at times flake off of the surface of the implant resulting in adverse health outcomes for the patient and instead are obtained for the biomaterial itself then such materials are even more desirable for the fabrication of medical devices.

Ideally, the antimicrobial agents that provide these antimicrobial properties would have a proven history of use and effectiveness activity against various microorganisms without any adverse effect on patients' health. The antimicrobial material, or other materials containing the antimicrobial additive, should be applicable to medical or other health care product and/or surface thereof by commercially-viable manufacturing methods such as molding, extrusion, and all other thermoplastic methods of 'conversion' or solvent-based processing, water-borne systems, and 100%-solids (crosslinkable) liquid. In addition, the antimicrobial additive should not interfere with the physiochemical and/or mechanical properties of the treated material, medical or other health care product and/or surface there.

Bacterial infection is a common complication related to the use of medical devices. Advances in various medical devices, including but not limited to catheters, vascular access devices, peripheral lines, intravenous (IV) sites, drains, gastric feeding tubes, trachea tubes, stents, guidewires, pacemakers, and other implantable devices, have benefited diagnostic and therapeutic medical care. However, bacterial infections are becoming a serious and common complication related to the use of medical devices, especially those implanted and/or used inside the patient's body.

One approach to reduce device-related infections is to develop surfaces with bactericidal activity, for example by making or coating the surface with a material that will elute and/or release antimicrobial compounds. Almost all treatments fall into one of the following three categories: 1) adsorption of the antimicrobial additive to the surface of materials passively or in combination with surfactants or by way of surface-bonded polymers; 2) incorporation of the antimicrobial additive into a polymer coating applied on the material surface; 3) compounding the antimicrobial additive into the bulk material comprising the device. However, all of these approaches have drawbacks.

Further many of the approaches for providing antimicrobial performance can be difficult to combine with effective non-fouling (i.e., non-thrombogenic) performance. Implantation of a medical device into a patient's body can result in various reactions to the device. Introduction of a material into contact with the blood generally causes coagulation and thrombosis. Additionally, the introduction of a material into a human body results in activation of the body's immune response, leading to acute and sometimes chronic inflammation. As such, much emphasis has been placed on the modification of the surfaces of biomaterials, in particular the surface modification of polymers, to decrease or eliminate the surface adsorption of proteins and improve their biocompatibility. Common approaches to surface modification of polymers has included plasma polymerized surfaces, surface coatings, grafting of polymers from or to the surface, and physical adsorption of surface modifying materials onto a polymer surface. Each of these methods, however, has significant drawbacks, including expense, difficulty of application to devices with intricate surface geometries, and imparting relatively fragile surface films. Thermoplastic polyurethanes (TPUs) are widely used as biomaterials owing to their excellent physical and mechanical properties. Surface modification of TPUs for biomedical applications has previously been accomplished by a variety of means, including coating the surface via dip coating or spray coating, or plasma polymerization of appropriate materials onto the surface of the TPU. Further, the addition of additives, such as fluorocarbons, which are non-compatible with the TPU and spontaneously migrate to the polymer surface, have been used to modify the polymer surface. Fluorocarbon surfaces, however, do not prevent fouling by all proteins. It would be desirable, then, to provide a surface-modified polymer having non-fouling and/or non-thrombogenic characteristics without post treatment following manufacture of the devices.

However, these different properties can sometimes interfere with one another and/or are not additive when combined. There is a need for compositions with good antimicrobial performance that are also non-fouling.

Therefore, a simple and cost effective method to create an antimicrobial composition is needed that is useful for medical applications, and which can also provide good non-fouling performance where the antimicrobial additive and the non-fouling additive do not interfere with each other.

SUMMARY

The disclosed technology provides thermoplastic polyurethane compositions having antimicrobial properties while still maintaining good physical properties and good non-fouling and/or non-thrombogenic properties, methods of making the same, and articles, including medical devices, made from such compositions. The disclosed technology includes a process of making an antimicrobial polymer composition, where the process includes mixing an antimicrobial additive into a base polymer and further includes mixing in a non-fouling additive, where the antimicrobial additive does not elute from the composition as indicated by a zero zone of inhibition on the AATCC 147 assay and the antimicrobial and non-fouling additives do not negatively impact each other's effectiveness to such an extent as to result in failure of the antimicrobial or thrombogencity tests.

By surface modification, as used herein, includes coating a surface via dip coating or spray coating, or plasma polymerization of appropriate materials onto the surface of the TPU, designing the composition so that certain additives, with desirable properties, spontaneously migrate (i.e. bloom) to the polymer surface, or any combination thereof.

The disclosed technology provides a surface modifying polymer composition, which includes: (a) an non-fouling additive comprising an oligomeric or polymeric additive formed from two or more of: (i) a zwitterionic monomer or a polyalkylene glycol monomer or combinations thereof; (ii) a silicone or fluorocarbon monomer, or combinations thereof; or (iii) an alkyl substituted methacrylate, acrylate, acrylamide, or vinyl monomer, or combinations thereof; (b) a base polymer comprising a polymer backbone; and (c) an antimicrobial additive comprising (i) a deprotonated guanidine compound where some portion of said deprotonated guanidine compound is covalently bonded into the polymeric backbone of said base polymer by isocyanate linkages, (ii) a protonated guanidine compound, where some portion of said protonated guanidine compound is hydrogen bonded to the polymeric backbone of said base polymer, or (iii) a combination thereof; wherein component (a) and component (c) are incorporated into the base polymer by melt processing or solvent processing.

The disclosed technology further provides an article that includes a surface modifying polymer composition, where the surface modifying polymer composition includes: (a) an non-fouling additive comprising an oligomeric or polymeric additive formed from two or more of: (i) a zwitterionic monomer or a polyalkylene glycol monomer or combinations thereof; (ii) a silicone or fluorocarbon monomer, or combinations thereof; or (iii) an alkyl substituted methacrylate, acrylate, acrylamide, or vinyl monomer, or combinations thereof; (b) a base polymer comprising a polymer backbone; and (c) an antimicrobial additive comprising (i) a deprotonated guanidine compound where some portion of said deprotonated guanidine compound is covalently bonded into the polymeric backbone of said base polymer by isocyanate linkages, (ii) a protonated guanidine compound, where some portion of said protonated guanidine compound is hydrogen bonded to the polymeric backbone of said base polymer, or (iii) a combination thereof; wherein component (a) and component (c) are incorporated into the base polymer by melt processing or solvent processing.

The disclosed technology provides the described composition and/or article where the deprotonated guanidine compound includes a deprotonated guanidine compound, a deprotonated biguanidine compound, or a mixture thereof. In some embodiments, the deprotonated guanidine compound is deprotonated PHMB.

The disclosed technology provides the described compositions, articles, and processes where the protonated guanidine compound includes a protonated guanidine compound, a protonated biguanidine compound, or a mixture thereof. In some embodiments, the protonated guanidine compound is protonated PHMB.

The disclosed technology provides the described composition and/or article where the base polymer includes a thermoplastic polyurethane derived from (a) diphenylmethane diisocyanate, (b) a polyether polyol, and (c) a butane diol component. In some embodiments, the base polymer includes a thermoplastic polyurethane derived from (a) hexamethylene diisocyanate or dicyclohexylmethane-4,4'-diisocyanate (H12MDI), (b) a polyether polyol, and (c) butane diol component.

The disclosed technology provides the described composition and/or article where the polymer composition is coated onto a material forming the article.

The disclosed technology provides the described composition and/or article where the polymer composition is coated onto a materials utilizing dip coating, roll to roll coating, spin coating or spray coating.

The disclosed technology provides the described composition and/or article where the article comprises a medical device, a personal care article, a pharmaceutical article, a health care product article, a food processing article or a marine article.

The disclosed technology provides the described composition and/or article where the article is a medical device that includes one or more of PICC catheter, a CVC catheter, an angiography catheter, an angioplasty catheter, a urology catheters, a catheter connector, or medical tubing.

The disclosed technology further provides for methods of making the described surface-modified polymer composition. Such methods include the steps of (I) forming (a) an oligomeric or polymeric additive comprising i) a zwitterionic monomer, or a polyalkylene glycol monomer or combinations thereof; ii) a silicone or fluorocarbon monomer, or combinations thereof; or iii) an alkyl substituted methacrylate, acrylate, acrylamide, or vinyl monomer, or combinations thereof; and (II) incorporating component (a), (b) a base polymer, and (c) an antimicrobial additive into one another; wherein said antimicrobial additive includes (i) a deprotonated guanidine or biguanidine compound where some portion of said deprotonated guanidine compound is covalently bonded into the polymeric backbone of said base polymer by linkages between the isocyanate group and nitrogen containing groups in the guanide or biguanide molecule, (ii) a protonated guanidine compound, where some portion of said protonated guanidine compound is hydrogen bonded to the polymeric backbone of said base polymer, or (iii) a combination thereof; and resulting in a surface-modified polymer composition with non-fouling/non-thrombogenic and antimicrobial properties.

The disclosed technology further provides for the described methods where the incorporation of components (a), (b), and (c) are accomplished by the melt processing of components (a) and (c) into (b) the base polymer.

The disclosed technology further provides for the described methods where the polymer composition is coated onto a material.

The disclosed technology further provides for the described methods where the polymer composition is coated onto the material utilizing a dip coating, a roll to roll coating, a spin coating or a spray coating process.

The disclosed technology further provides for the described methods where the methods further include the step of annealing. In some embodiments, the annealing is performed at a temperature of from about 50° C. to about 150° C. for a time of about 2 hours up to about 72 hours.

The disclosed technology further provides for compositions made by the described methods and used to make the described articles.

DETAILED DESCRIPTION

Various preferred features and embodiments will be described below by way of non-limiting illustration.

The disclosed technology provides a surface modified polymer composition that includes a bloom-promoting monomer, a non-fouling monomer, an adherence-promoting monomer, and combinations thereof. In one embodiment, the polymer composition includes a) an oligomeric or polymeric additive formed from one or more of i) a phosphorylcholine, a carboxybetaine, a sulfo betaine or a polyalkylene glycol monomer or combinations thereof; ii) a silicone or fluorocarbon monomer, or combinations thereof; and iii) an alkyl substituted monomer; and b) a base polymer.

The Oligomeric or Polymeric Additive

The surface-modified polymer composition as disclosed herein includes an oligomeric or polymeric additive formed from i) a zwitterionic monomer. In one embodiment, the zwitterionic monomer includes one or more of a phosphorylcholine, a carboxybetaine, a sulfobetaine, or a polyalkylene glycol monomer.

The additive of the invention can be oligomeric or polymeric. In one embodiment, the additive includes dimers, trimers, or tetramers. In one embodiment, the additive includes a block, a graft or a branched polymer or copolymer. In one embodiment, the oligomeric or polymeric additive has a molecular weight (Mn) of from about 1,000 to about 50,000 daltons. In one embodiment, the additive has a molecular weight of from about 2,000 to about 15,000 daltons.

The Zwitterionic Monomer

In one embodiment, the additive of the composition can include a non-fouling monomer. The non-fouling monomer can include a zwitterionic monomer or a polyalkylene glycol monomer. In one embodiment, the additive of the composition as disclosed herein includes a zwitterionic monomer or a polyalkylene glycol monomer. The zwitterionic monomer can include one or more of a phosphorylcholine, a carboxybetaine or a sulfobetaine monomer, derivatives thereof, or combinations thereof. Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer includes a phosphorylcholine moiety, a sulfobetaine moiety, a carboxy betaine moiety, derivatives thereof, or combinations thereof. In one embodiment, the zwitterionic monomer includes 2-hydroxyethyl methacrylate phosphorylcholine.

The sulfobetaine monomer can be selected from one or more of sulfobetaine acrylates, sulfobetaine acrylamides, sulfobetaine vinyl compounds, sulfobetaine epoxides, and mixtures thereof. In one embodiment, the monomer is a methacrylate monomer which incorporates a sulfobetaine group.

The carboxybetaine monomer can include carboxybetaine acrylates, carboxybetaine acrylamides, carboxybetaine vinyl compounds, carboxybetaine epoxides, and mixtures thereof. In one embodiment, the monomer is carboxybetaine methacrylate.

In some embodiments, the zwitterionic monomers incorporated into the oligomeric or polymeric additives are present in an amount from about 10-40 mole percent of the total monomer composition of the additive.

The Polyalkylene Glycol Monomer

In one embodiment, the oligomeric or polymeric additive can further include a polyalkylene glycol monomer. In a further embodiment, the oligomeric or polymeric additive can alternatively include a polyalkylene glycol monomer, where the polyalkylene glycol monomer is utilized in place of the zwitterionic monomer. Suitable polyalkylene glycol monomers include, but are not limited to acrylate, methacrylate esters of polyether polyols having a total of from about 2 to about 100 carbon atoms. Useful commercial polyalkylene glycol monomers include poly(ethylene glycol) comprising ethylene oxide reacted with ethylene glycol or other alcohol, such as poly(ethylene glycol) methyl ether methacrylate/acrylate with various molecular weights, glycol butyl ether methacrylate/acrylate with various molecular weights, poly(ethylene glycol) methacrylate/acrylate with various molecular weights. In some embodiments, the polyalkylene glycol monomer can be present in an amount from about 10 mole % to about 50 mole % of the total monomer composition of the additive.

The Silicone or Fluorocarbon Monomer

The oligomeric or polymeric additive of the surface-modified polymer composition disclosed herein can include a bloom-promoting monomer. The bloom-promoting monomer can include a silicone or fluorocarbon monomer, or combinations thereof.

In one embodiment, the silicone monomer includes a functionalized polysiloxane. The functionalized polysiloxane can be mono- or multi-functionalized. Suitable examples of functionalized polysiloxane include mono- or multi-functionalized acrylate, methacrylate, vinyl or allyl functionalized polysiloxanes, such a mono vinyl terminated polydimethylsiloxanes; mono methacryloxypropyl terminated polydimethylsiloxanes, vinyl terminated trifluoropropylmethylsiloxane; and monoallyl-mono trimethylsiloxy terminated polyethylene oxide. The polysiloxanes may generally have a molecular weight (Mn) of from about 100 to about 100,000 Da. The functional groups may be terminal, internal, or terminal and internal.

The functional polysiloxane may be represented by the following formula: A-B-C wherein, A is a polymerizable group selected from vinyl, acrylate, or methacrylate or an active hydrogen group selected from an alcohol, an amine or a thiol; B is an optional linking group, and C is a polysiloxane group.

Functionalized polysiloxanes which are useful in the additives of the invention are available commercially from a variety of sources. For example, terminally functionalized polysiloxanes, including linear organofunctional polydimethylsiloxanes, are available from Evonik Industries under the Tegomer® range of products, including Tegomer® C-Si 2342 (Dicarboxyalkylpolydimethylsiloxane), Tegomer E-Si 2330 (Diepoxyalkylpolydimethylsiloxane), Tegomer®H-Si 2315 (Dihydroxyalkylpolydimethylsiloxane), and Tegomer® V-Si (Diacryloxypolydimethylsiloxane). Gelest Inc. also has various functional polysiloxane such as MCR-C12,18,22 series (MonoCarbinol Terminated polyDimethylsiloxane), MCR-C61,62 (MonoDiCarbinol Terminated PolyDimethylsiloxane), PDV series (Vinyl Terminated Diphenylsiloxane-Dimethylsiloxane Copolymers) FMV (Vinyl Terminated TrifluoropropylMethylsiloxane-Dimethylsiloxane Copolymer), CMS ((Carbinol functional)Methyl siloxane-Dimethylsiloxane Copolymers).

In some embodiments, the oligomeric or polymeric additive can include a fluorocarbon monomer. The fluorocarbon monomer may be represented by the following formula: D-E-F wherein, D is a polymerizable group selected from acrylate, methacrylate or vinyl or an active hydrogen group selected from an alcohol, an amine or a thiol, E is an optional linking group; and F is fluorocarbon group which can be perfluorinated or partially fluorinated.

Suitable fluorocarbon monomers include, but are not limited to 1,1,1,3,3,3-hexafluoroisopropyl acrylate, 1,1,1,3,3,3-hexafluoroisopropyl methacrylate, 2,2,3,4,4,4-hexafluorobutyl methacrylate, 2,2,3,3-tetrafluoropropyl methacrylate, 2,2,2-trifluoroethyl methacrylate, 2,2,3,3,4,4,4-heptafluorobutyl acrylate, 2,2,3,3,4,4,4-Heptafluorobutyl methacrylate, 2,2,3,3,3-Pentafluoropropyl acrylate, 2,2,3,3,4,4,5,5-Octafluoropentyl methacrylate, 2,2,3,3,3-Pentafluoropropyl methacrylate, 3,3,4,4,5,5,6,6,7,7,8,8,8-Tridecafluorooctyl methacrylate, 3,3,4,4,5,5,6,6,7,7,8,8,9,9,10,10,10-Heptadecafluorodecyl methacrylate, 3,3,4,4,5,5,6,6,7,7,8,8,8-Tridecafluorooctyl acrylate, 3,3,4,4,5,5,6,6,7,7,8,8,9,9,10,10,11,11,12,12,12-Heneicosafluorododecyl acrylate, 2,2,3,3,4,4,5,5-Octafluoropentyl acrylate, 2,2,3,3,4,4,5,5,6,6,7,7-Dodecafluoroheptyl acrylate 95%, 2,2,3,4,4,4-Hexafluorobutyl acrylate, 1H,1H,2H,2H-Perfluorodecyl acrylate, 2-[(1',1',1'-Trifluoro-2'-(trifluoromethyl)-2'-hydroxy)propyl]-3-norbornyl methacrylate, 1,1,1-Trifluoro-2-(trifluoromethyl)-2-hydroxy-4-methyl-5-pentyl methacrylate, 2-(Perfluorohexyl)ethyl methacrylate, Perfluorohexylethyl alcohol, 4-Vinylbenzyl Hexafluoroisopropyl Ether, 4-Vinylbenzyl Perfluorooctanoate, 4-Vinylbenzyl Trifluoroacetate, Allyl Heptafluorobutyrate, Allyl Perfluoroheptanoate, Allyl Perfluorononanoate, Allyl Perfluorooctanoate, Allyl Tetrafluoroethyl Ether, Allyl Trifluoroacetate, and Allylpentafluorobenzene The silicone or fluorocarbon monomer can be present, in one embodiment, in an amount from about 5% to about 40% of the total monomer composition of the additive.

The Alkyl Substituted Monomer

In some embodiments, the oligomeric or polymeric additive includes an adhesion-promoting monomer. The adhesion-promoting monomer can include an alkyl substituted monomer. In one embodiment, the alkyl substituted monomer includes a methacrylate, an acrylate, an acrylamide or a vinyl monomer, or combinations thereof. Suitable monomers include, but are not limited to, substituted acrylates and methacrylates such as methyl methacrylate, ethyl acrylate, butyl acrylate, butyl methacrylate, 2-ethylhexylmethacrylate, and other similar monomers which will be readily obvious to those skilled in the art. The monomer may be chosen such that, when included in the additive, it will increase the affinity of the additive to the base polymer. In some embodiments, the alkyl substituted monomer will be present in the additive in an amount of from about 10 mole % to about 70 mole % of the total monomer composition of the additive.

In some embodiments, the alkyl substituted monomer can include hydroxyalkyl acrylates, acrylates with primary, secondary, or tertiary amino groups, and reactive or crosslinkable acrylate, such as acrylates containing silyl groups, double bonds, or other reactive functional groups; acrylamides, including substituted acrylamides as described above for acrylates; vinyl compounds; multifunctional molecules, such as di-, tri-, and tetraisocyanates, di-, tri-, and tetraols, di-, tri-, and tetraamines, and di-, tri-, and tetrathiocyanates; cyclic monomers, such as lactones and lactams; and combinations thereof; Alkyl methacrylates or other hydrophobic methacrylates, such as ethyl methacrylate, butyl methacrylate, hexyl methacrylate, 2-ethylhexyl methacrylate, methyl methacrylate, lauryl methacrylate, isobutyl methacrylate, isodecyl methacrylate, phenyl methacrylate, decyl methacrylate, 3,3,5-trimethylcyclohexyl methacrylate, benzyl methacrylate, cyclohexyl methacrylate, stearyl methacrylate, tert-butyl methacrylate, tridecyl methacrylate, and 2-naphthyl methacrylate; Reactive or crosslinkable methacrylates, such as 2-(trimethylsilyloxy)-ethylmethacrylate, 3-(trichlorosilyl)propyl methacrylate, 3-(trimethoxysilyl)-propyl methacrylate, 3-[tris(trimethylsiloxy)silyl]propyl methacrylate, trimethylsilyl methacrylate, allyl methacrylate, vinyl methacrylate, 3-(acryloyloxy)-2-hydroxypropyl methacrylate, 3-(diethoxymethylsilyl)propyl methacrylate, 3-(dimethylchlorosilyl)propyl methacrylate, isocyanates, such as 2-isocyanatoethyl methacrylate, glycidyl methacrylate, 2-hydroxyethyl methacrylate, 3-chloro-2-hydroxypropyl methacrylate, Hydroxybutyl methacrylate, glycol methacrylate, hydroxypropyl methacrylate, and 2-hydroxypropyl 2-(methacryloyloxy)ethyl phthalate.

The amount of the various monomers used to make the additives of the invention are typically in the range of 10-60 mole percent of the total additive composition. The amount of each particular monomer which is useful in the invention will depend on which specific monomer from each class of monomers is used and the base polymer into which the additive is being blended. For example, for a PTMEG based aromatic TPU, additives which contain from about 10 to about 30 mole percent of a fluorocarbon methacrylates, from about 10 to about 30 percent of polyethyleneglycol methacrylate and from about 40 to about 80 percent of methylmethacrylate has been shown to be effective to impart non-fouling and/or non-thrombogenic surfaces to the TPU base polymer with which it is blended.

Synthesis of Oligomeric or Polymeric Additives

The oligomeric or polymeric additive as disclosed herein may be formed via addition polymerization (radical, cationic and ionic) or condensation polymerization. In one embodiment, the additive is formed using addition polymerization, in which, for example, mixed monomer solution and radical initiator are metered into a reactor to allow the reaction for approximately over 4 hours and allowed to post-react for an additional 14 hours. The reaction temperature and time will be dependent on the initiator used. For example, for AIBN the reaction temperature is 70 C and the time are as given above. The additives are then recovered by stripping off solvent.

In one embodiment, the additive is formed using condensation polymerization, in which, for example, a diisocyanate is allowed to react with Tegomer® (a diol monomer available from Evonik with a pendant PEG group) to form a prepolymer with free terminal isocyanate groups. Monofunctional fluorinated or polysiloxanes such as Capstone®

62AL (available from DuPont) react with prepolymers to end-cap the prepolymer to form oligomeric/polymeric additives with urethane and/or urea bonds.

The Base Polymer

The surface modified polymer compositions described herein include a base polymer. In some embodiments, the base polymer includes a thermoplastic polyurethane, a Nylon, a polyethylene, a polyester, a polyvinylchloride, a polysulfone, a polysiloxane, a polypropylene, a polycarbonate, and combinations thereof.

In one embodiment, the base polymer is a thermoplastic polyurethane. The TPU compositions described herein are made using: (a) a polyisocyanate. (b) a polyol; and optionally (a chain extender). The TPU may be present in the surface modified polymer in an amount from about 80 to about 99.9 wt. percent.

The Polyisocyanate

The TPU compositions described herein are made using a) a polyisocyanate component. The polyisocyanate and/or polyisocyanate component includes one or more polyisocyanates. In some embodiments, the polyisocyanate component includes one or more diisocyanates.

In some embodiments, the polyisocyanate and/or polyisocyanate component includes an α, ω-alkylene diisocyanate having from about 5 to about 20 carbon atoms.

Suitable polyisocyanates include aromatic diisocyanates, aliphatic diisocyanates, or combinations thereof. In some embodiments, the polyisocyanate component includes one or more aromatic diisocyanates. In some embodiments, the polyisocyanate component is essentially free of, or even completely free of, aliphatic diisocyanates. In other embodiments, the polyisocyanate component includes one or more aliphatic diisocyanates. In some embodiments, the polyisocyanate component is essentially free of, or even completely free of, aromatic diisocyanates.

Examples of useful polyisocyanates include aromatic diisocyanates such as 4,4'-methylenebis(phenyl isocyanate) (MDI), m-xylene diisocyanate (XDI), phenylene-1,4-diisocyanate, naphthalene-1,5-diisocyanate, and toluene diisocyanate (TDI); as well as aliphatic diisocyanates such as isophorone diisocyanate (IPDI), 1,4-cyclohexyl diisocyanate (CHDI), decane-1,10-diisocyanate, lysine diisocyanate (LDI), 1,4-butane diisocyanate (BDI), isophorone diisocyanate (IPDI), 3,3'-dimethyl-4,4'-biphenylene diisocyanate (TODI), 1,5-naphthalene diisocyanate (NDI), and dicyclohexylmethane-4,4'-diisocyanate (H12MDI). Mixtures of two or more polyisocyanates may be used. In some embodiments, the polyisocyanate is MDI and/or H12MDI. In some embodiments, the polyisocyanate includes MDI. In some embodiments, the polyisocyanate includes H12MDI.

In some embodiments, the thermoplastic polyurethane is prepared with a polyisocyanate component that includes H12MDI. In some embodiments, the thermoplastic polyurethane is prepared with a polyisocyanate component that consists essentially of H12MDI. In some embodiments, the thermoplastic polyurethane is prepared with a polyisocyanate component that consists of H12MDI.

In some embodiments, the thermoplastic polyurethane is prepared with a polyisocyanate component that includes (or consists essentially of, or even consists of) H12MDI and at least one of MDI, HDI, TDI, IPDI, LDI, BDI, PDI, CHDI, TODI, and NDI.

In some embodiments, the polyisocyanate used to prepare the TPU and/or TPU compositions described herein is at least 50%, on a weight basis, a cycloaliphatic diisocyanate.

In some embodiments, the polyisocyanate includes an α, ω-alkylene diisocyanate having from about 5 to 20 carbon atoms.

In some embodiments, the polyisocyanate used to prepare the TPU and/or TPU compositions described herein includes hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate, or combinations thereof.

The Polyol Component

The TPU compositions described herein are made using: (b) a polyol component.

Polyols include polyether polyols, polyester polyols, polycarbonate polyols, polysiloxane polyols, and combinations thereof.

Suitable polyols, which may also be described as hydroxyl terminated intermediates, when present, may include one or more hydroxyl terminated polyesters, one or more hydroxyl terminated polyethers, one or more hydroxyl terminated polycarbonates, one or more hydroxyl terminated polysiloxanes, or mixtures thereof.

Suitable hydroxyl terminated polyester intermediates include linear polyesters having a number average molecular weight (Mn) of from about 500 to about 10,000, from about 700 to about 5,000, or from about 700 to about 4,000, and generally have an acid number less than 1.3 or less than 0.5. The molecular weight is determined by assay of the terminal functional groups and is related to the number average molecular weight. The polyester intermediates may be produced by (1) an esterification reaction of one or more glycols with one or more dicarboxylic acids or anhydrides or (2) by transesterification reaction, i.e., the reaction of one or more glycols with esters of dicarboxylic acids. Mole ratios generally in excess of more than one mole of glycol to acid are preferred so as to obtain linear chains having a preponderance of terminal hydroxyl groups. Suitable polyester intermediates also include various lactones such as polycaprolactone typically made from ε-caprolactone and a bifunctional initiator such as diethylene glycol. The dicarboxylic acids of the desired polyester can be aliphatic, cycloaliphatic, aromatic, or combinations thereof. Suitable dicarboxylic acids which may be used alone or in mixtures generally have a total of from about 4 to about 15 carbon atoms and include: succinic, glutaric, adipic, pimelic, suberic, azelaic, sebacic, dodecanedioic, isophthalic, terephthalic, cyclohexane dicarboxylic, and the like. Anhydrides of the above dicarboxylic acids such as phthalic anhydride, tetrahydrophthalic anhydride, or the like, can also be used. Adipic acid is a preferred acid. The glycols which are reacted to form a desirable polyester intermediate can be aliphatic, aromatic, or combinations thereof, including any of the glycols described above in the chain extender section, and have a total of from about 2 to about 20 or from about 2 to about 12 carbon atoms. Suitable examples include ethylene glycol, 1,2-propanediol, 1,3-propanediol, 1,3-butanediol, 1,4-butanediol, 1,5-pentanediol, 1,6-hexanediol, 2,2-dimethyl-1,3-propanediol, 1,4-cyclohexanedimethanol, decamethylene glycol, dodecamethylene glycol, and mixtures thereof.

The polyol component may also include one or more polycaprolactone polyester polyols. The polycaprolactone polyester polyols useful in the technology described herein include polyester diols derived from caprolactone monomers. The polycaprolactone polyester polyols are terminated by primary hydroxyl groups. Suitable polycaprolactone polyester polyols may be made from ε-caprolactone and a bifunctional initiator such as diethylene glycol, 1,4-butanediol, or any of the other glycols and/or diols listed herein. In some embodiments, the polycaprolactone polyester polyols are linear polyester diols derived from caprolactone monomers.

Useful examples include CAPA™ 2202A, a 2,000 number average molecular weight (Mn) linear polyester diol, and CAPA™ 2302A, a 3,000 Mn linear polyester diol, both of which are commercially available from Perstorp Polyols Inc. These materials may also be described as polymers of 2-oxepanone and 1,4-butanediol.

The polycaprolactone polyester polyols may be prepared from 2-oxepanone and a diol, where the diol may be 1,4-butanediol, diethylene glycol, monoethylene glycol, 1,6-hexanediol, 2,2-dimethyl-1,3-propanediol, or any combination thereof. In some embodiments, the diol used to prepare the polycaprolactone polyester polyol is linear. In some embodiments, the polycaprolactone polyester polyol is prepared from 1,4-butanediol. In some embodiments, the polycaprolactone polyester polyol has a number average molecular weight from 500 to 10,000, or from 500 to 5,000, or from 1,000 or even 2,000 to 4,000 or even 3,000.

Suitable hydroxyl terminated polyether intermediates include polyether polyols derived from a diol or polyol having a total of from 2 to 15 carbon atoms, in some embodiments an alkyl diol or glycol which is reacted with an ether comprising an alkylene oxide having from 2 to 6 carbon atoms, typically ethylene oxide or propylene oxide or mixtures thereof. For example, hydroxyl functional polyether can be produced by first reacting propylene glycol with propylene oxide followed by subsequent reaction with ethylene oxide. Primary hydroxyl groups resulting from ethylene oxide are more reactive than secondary hydroxyl groups and thus are preferred. Useful commercial polyether polyols include poly(ethylene glycol) comprising ethylene oxide reacted with ethylene glycol, poly(propylene glycol) comprising propylene oxide reacted with propylene glycol, poly(tetramethylene ether glycol) comprising water reacted with tetrahydrofuran which can also be described as polymerized tetrahydrofuran, and which is commonly referred to as PTMEG. In some embodiments, the polyether intermediate includes PTMEG. Suitable polyether polyols also include polyamide adducts of an alkylene oxide and can include, for example, ethylenediamine adduct comprising the reaction product of ethylenediamine and propylene oxide, diethylenetriamine adduct comprising the reaction product of diethylenetriamine with propylene oxide, and similar polyamide type polyether polyols. Copolyethers can also be utilized in the described compositions. Typical copolyethers include the reaction product of THF and ethylene oxide or THF and propylene oxide. These are available from BASF as PolyTHF® B, a block copolymer, and PolyTHF® R, a random copolymer. The various polyether intermediates generally have a number average molecular weight (Mn) as determined by assay of the terminal functional groups which is an average molecular weight greater than about 700, such as from about 700 to about 10,000, from about 1,000 to about 5,000, or from about 1,000 to about 2,500. In some embodiments, the polyether intermediate includes a blend of two or more different molecular weight polyethers, such as a blend of 2,000 Mn and 1,000 Mn PTMEG.

Suitable hydroxyl terminated polycarbonates include those prepared by reacting a glycol with a carbonate. U.S. Pat. No. 4,131,731 is hereby incorporated by reference for its disclosure of hydroxyl terminated polycarbonates and their preparation. Such polycarbonates are linear and have terminal hydroxyl groups with essential exclusion of other terminal groups. The essential reactants are glycols and carbonates. Suitable glycols are selected from cycloaliphatic and aliphatic diols containing 4 to 40, and or even 4 to 12 carbon atoms, and from polyoxyalkylene glycols containing 2 to 20 alkoxy groups per molecule with each alkoxy group containing 2 to 4 carbon atoms. Suitable diols include aliphatic diols containing 4 to 12 carbon atoms such as 1,4-butanediol, 1,5-pentanediol, neopentyl glycol, 1,6-hexanediol, 2,2,4-trimethyl-1,6-hexanediol, 1,10-decanediol, hydrogenated dilinoleylglycol, hydrogenated dioleylglycol, 3-methyl-1,5-pentanediol; and cycloaliphatic diols such as 1,3-cyclohexanediol, 1,4-dimethylolcyclohexane, 1,4-cyclohexanediol-, 1,3-dimethylolcyclohexane-, 1,4-endomethylene-2-hydroxy-5-hydroxymethyl cyclohexane, and polyalkylene glycols. The diols used in the reaction may be a single diol or a mixture of diols depending on the properties desired in the finished product. Polycarbonate intermediates which are hydroxyl terminated are generally those known to the art and in the literature. Suitable carbonates are selected from alkylene carbonates composed of a 5 to 7 member ring. Suitable carbonates for use herein include ethylene carbonate, trimethylene carbonate, tetramethylene carbonate, 1,2-propylene carbonate, 1,2-butylene carbonate, 2,3-butylene carbonate, 1,2-ethylene carbonate, 1,3-pentylene carbonate, 1,4-pentylene carbonate, 2,3-pentylene carbonate, and 2,4-pentylene carbonate. Also, suitable herein are dialkylcarbonates, cycloaliphatic carbonates, and diarylcarbonates. The dialkylcarbonates can contain 2 to 5 carbon atoms in each alkyl group and specific examples thereof are diethylcarbonate and dipropylcarbonate. Cycloaliphatic carbonates, especially dicycloaliphatic carbonates, can contain 4 to 7 carbon atoms in each cyclic structure, and there can be one or two of such structures. When one group is cycloaliphatic, the other can be either alkyl or aryl. On the other hand, if one group is aryl, the other can be alkyl or cycloaliphatic. Examples of suitable diarylcarbonates, which can contain 6 to 20 carbon atoms in each aryl group, are diphenyl carbonate, ditolylcarbonate, and dinaphthylcarbonate.

Suitable polysiloxane polyols include α-ω-hydroxyl or amine or carboxylic acid or thiol or epoxy terminated polysiloxanes. Examples include poly(dimethylsiloxane) terminated with a hydroxyl or amine or carboxylic acid or thiol or epoxy group. In some embodiments, the polysiloxane polyols are hydroxyl terminated polysiloxanes. In some embodiments, the polysiloxane polyols have a number-average molecular weight in the range from 300 to 5,000, or from 400 to 3,000.

Polysiloxane polyols may be obtained by the dehydrogenation reaction between a polysiloxane hydride and an aliphatic polyhydric alcohol or polyoxyalkylene alcohol to introduce the alcoholic hydroxy groups onto the polysiloxane backbone.

In some embodiments, the polysiloxane polyols may be represented by one or more compounds having the following formula:

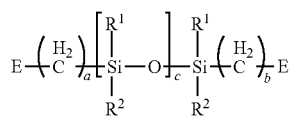

in which: each R1 and R2 are independently a 1 to 4 carbon atom alkyl group, a benzyl, or a phenyl group; each E is OH or NHR$^3$ where R$^3$ is hydrogen, a 1 to 6 carbon atoms alkyl group, or a 5 to 8 carbon atoms cyclo-alkyl group; a and b are each independently an integer from 2 to 8; c is an integer from 3 to 50. In amino-containing polysiloxanes, at least one of the E groups is $NHR^3$. In the hydroxyl-containing polysiloxanes, at least one of the E groups is OH. In some embodiments, both $R^1$ and $R^2$ are methyl groups.

Suitable examples include α,ω-hydroxypropyl terminated poly(dimethysiloxane) and α,ω-amino propyl terminated poly(dimethysiloxane), both of which are commercially available materials. Further examples include copolymers of the poly(dimethysiloxane) materials with a poly(alkylene oxide).

The polyol component, when present, may include poly(ethylene glycol), poly(tetramethylene ether glycol), poly(trimethylene oxide), ethylene oxide capped poly(propylene glycol), poly(butylene adipate), poly(ethylene adipate), poly(hexamethylene adipate), poly(tetramethylene-co-hexamethylene adipate), poly(3-methyl-1,5-pentamethyl ene adipate), polycaprolactone diol, poly(hexamethylene carbonate) glycol, poly(pentamethylene carbonate) glycol, poly(trimethylene carbonate) glycol, dimer fatty acid based polyester polyols, vegetable oil based polyols, or any combination thereof.

Examples of dimer fatty acids that may be used to prepare suitable polyester polyols include Priplast™ polyester glycols/polyols commercially available from Croda and Radia® polyester glycols commercially available from Oleon.

In some embodiments, the polyol component includes a polyether polyol, a polycarbonate polyol, a polycaprolactone polyol, or any combination thereof.

In some embodiments, the polyol component includes a polyether polyol. In some embodiments, the polyol component is essentially free of or even completely free of polyester polyols. In some embodiments, the polyol component used to prepare the TPU is substantially free of, or even completely free of polysiloxanes.

In some embodiments, the polyol component includes hydroxyl terminated telechelic oligomers of ethylene oxide, propylene oxide, butylene oxide, styrene oxide, poly(tetramethylene ether glycol), poly(propylene glycol), poly(ethylene glycol), copolymers of poly(ethylene glycol) and poly(propylene glycol), epichlorohydrin, and the like, or combinations thereof. In some embodiments the polyol component includes poly(tetramethylene ether glycol).

The Chain Extender

The TPU compositions described herein are made using c) a chain extender component. Chain extenders include diols, diamines, and combination thereof.

Suitable chain extenders include relatively small polyhydroxy compounds, for example lower aliphatic or short chain glycols having from 2 to 20, or 2 to 12, or 2 to 10 carbon atoms. Suitable examples include ethylene glycol, diethylene glycol, propylene glycol, dipropylene glycol, 1,4-butanediol (BDO), 1,6-hexanediol (HDO), 1,3-butanediol, 1,5-pentanediol, neopentylglycol, 1,4-cyclohexanedimethanol (CHDM), 2,2-bis[4-(2-hydroxyethoxy) phenyl] propane (HEPP), hexamethylenediol, heptanediol, nonanediol, dodecanediol, 3-methyl-1,5-pentanediol, ethylenediamine, butanediamine, hexamethylenediamine, and hydroxyethyl resorcinol (HER), and the like, as well as mixtures thereof. In some embodiments, the chain extender includes BDO, HDO, 3-methyl-1,5-pentanediol, or a combination thereof. In some embodiments, the chain extender includes BDO. Other glycols, such as aromatic glycols could be used, but in some embodiments the TPUs described herein are essentially free of or even completely free of such materials.

In some embodiments, the chain extender used to prepare the TPU is substantially free of, or even completely free of, 1,6-hexanediol. In some embodiments, the chain extender used to prepare the TPU includes a cyclic chain extender. Suitable examples include CHDM, HEPP, HER, and combinations thereof. In some embodiments, the chain extender used to prepare the TPU includes an aromatic cyclic chain extender, for example HEPP, HER, or a combination thereof. In some embodiments, the chain extender used to prepare the TPU includes an aliphatic cyclic chain extender, for example CHDM. In some embodiments, the chain extender used to prepare the TPU is substantially free of, or even completely free of aromatic chain extenders, for example aromatic cyclic chain extenders. In some embodiments, the chain extender used to prepare the TPU is substantially free of, or even completely free of polysiloxanes.

In some embodiments, the chain extender component includes 1,4-butanediol, 2-ethyl-1,3-hexanediol, 2,2,4-trimethyl pentane-1,3-diol, 1,6-hexanediol, 1,4-cyclohexane dimethylol, 1,3-propanediol, 3-methyl-1,5-pentanediol or combinations thereof. In some embodiments, the chain extender component includes 1,4-butanediol, 3-methyl-1,5-pentanediol or combinations thereof. In some embodiments, the chain extender component includes 1,4-butanediol.

The described compositions include the TPU materials described above and also TPU compositions that include such TPU materials and one or more additional components. These additional components include other polymeric materials that may be blended with the TPU described herein. These additional components also include one or more additives that may be added to the TPU, or blend containing the TPU, to impact the properties of the composition.

The TPU described herein may also be blended with one or more other polymers. The polymers with which the TPU described herein may be blended are not overly limited. In some embodiments, the described compositions include two or more of the described TPU materials. In some embodiments, the compositions include at least one of the described TPU materials and at least one other polymer, which is not one of the described TPU materials. In some embodiments, the described blends will have the same combination of properties described above for the TPU composition. In other embodiments, the TPU composition will of course have the described combination of properties, while the blend of the TPU composition with one or more of the other polymeric materials described above may or may not.

Polymers that may be used in combination with the TPU materials described herein also include more conventional TPU materials such as non-caprolactone polyester-based TPU, polyether-based TPU, or TPU containing both non-caprolactone polyester and polyether groups. Other suitable materials that may be blended with the TPU materials described herein include polycarbonates, polyolefins, styrenic polymers, acrylic polymers, polyoxymethylene polymers, polyamides, polyphenylene oxides, polyphenylene sulfides, polyvinylchlorides, chlorinated polyvinylchlorides, polylactic acids, or combinations thereof.

Polymers for use in the blends described herein include homopolymers and copolymers. Suitable examples include: (i) a polyolefin (PO), such as polyethylene (PE), polypropylene (PP), polybutene, ethylene propylene rubber (EPR), polyoxyethylene (POE), cyclic olefin copolymer (COC), or combinations thereof; (ii) a styrenic, such as polystyrene (PS), acrylonitrile butadiene styrene (ABS), styrene acrylonitrile (SAN), styrene butadiene rubber (SBR or HIPS), polyalphamethylstyrene, styrene maleic anhydride (SMA), styrene-butadiene copolymer (SBC) (such as styrene-butadiene-styrene copolymer (SBS) and styrene-ethyl ene/butadiene-styrene copolymer (SEBS)), styrene-ethylene/propylene-styrene copolymer (SEPS), styrene butadiene latex (SBL), SAN modified with ethylene propylene diene monomer (EPDM) and/or acrylic elastomers (for example, PS-SBR copolymers), or combinations thereof; (iii) a thermoplastic polyurethane (TPU) other than those described above; (iv) a polyamide, such as Nylon™, including polyamide 6,6 (PA66), polyamide 1,1 (PA11), polyamide 1,2 (PA12), a copolyamide (COPA), or combinations thereof; (v) an acrylic polymer, such as polymethyl acrylate, polymethylmethacrylate, a methyl methacrylate styrene (MS) copolymer, or combinations thereof; (vi) a polyvinylchloride (PVC), a chlorinated polyvinylchloride (CPVC), or combinations thereof; (vii) a polyoxyemethylene, such as polyacetal; (viii) a polyester, such as polyethylene terephthalate (PET), polybutylene terephthalate (PBT), copolyesters and/or polyester elastomers (COPE) including polyether-ester block copolymers such as glycol modified polyethylene terephthalate (PETG), polylactic acid (PLA), polyglycolic acid (PGA), copolymers of PLA and PGA, or combinations thereof; (ix) a polycarbonate (PC), a polyphenylene sulfide (PPS), a polyphenylene oxide (PPO), or combinations thereof; or combinations thereof.

In some embodiments, these blends include one or more additional polymeric materials selected from groups (i), (iii), (vii), (viii), or some combination thereof. In some embodiments, these blends include one or more additional polymeric materials selected from group (i). In some embodiments, these blends include one or more additional polymeric materials selected from group (iii). In some embodiments, these blends include one or more additional polymeric materials selected from group (vii). In some embodiments, these blends include one or more additional polymeric materials selected from group (viii).

The additional additives suitable for use in the TPU compositions described herein are not overly limited. Suitable additives include pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, antimicrobials, radio-opaque additives, for example, barium sulfate, bismuth subcarbonate, bismuth trioxide, bismuth oxychloride, tantalum, and tungsten, amongst others, and any combination thereof.

In some embodiments, the additional component is a flame retardant. Suitable flame retardants are not overly limited and may include a boron phosphate flame retardant, a magnesium oxide, a dipentaerythritol, a polytetrafluoroethylene (PTFE) polymer, or any combination thereof. In some embodiments, this flame retardant may include a boron phosphate flame retardant, a magnesium oxide, a dipentaerythritol, or any combination thereof. A suitable example of a boron phosphate flame retardant is BUDIT®-326, commercially available from Budenheim USA, Inc. When present, the flame retardant component may be present in an amount from 0 to 10 weight percent of the overall TPU composition, in other embodiments from 0.5 to 10, or from 1 to 10, or from 0.5 or 1 to 5, or from 0.5 to 3, or even from 1 to 3 weight percent of the overall TPU composition.

The TPU compositions described herein may also include additional additives, which may be referred to as a stabilizer. The stabilizers may include antioxidants such as phenolics, phosphites, thioesters, and amines, light stabilizers such as hindered amine light stabilizers and benzothiazole UV absorbers, and other process stabilizers and combinations thereof. In one embodiment, the preferred stabilizer is Irganox®-1010 from BASF and Naugard®-445 from Chemtura. The stabilizer is used in the amount from about 0.1 weight percent to about 5 weight percent, in another embodiment from about 0.1 weight percent to about 3 weight percent, and in another embodiment from about 0.5 weight percent to about 1.5 weight percent of the TPU composition.

In addition, various conventional inorganic flame retardant components may be employed in the TPU composition. Suitable inorganic flame retardants include any of those known to one skilled in the art, such as metal oxides, metal oxide hydrates, metal carbonates, ammonium phosphate, ammonium polyphosphate, calcium carbonate, antimony oxide, clay, mineral clays including talc, kaolin, wollastonite, nanoclay, montmorillonite clay which is often referred to as nano-clay, and mixtures thereof. In one embodiment, the flame retardant package includes talc. The talc in the flame retardant package promotes properties of high limiting oxygen index (LOI). The inorganic flame retardants may be used in the amount from 0 to about 30 weight percent, from about 0.1 weight percent to about 20 weight percent, in another embodiment about 0.5 weight percent to about 15 weight percent of the total weight of the TPU composition.

Still further optional additives may be used in the TPU compositions described herein. The additives include colorants, antioxidants (including phenolics, phosphites, thioesters, and/or amines), antiozonants, stabilizers, inert fillers, lubricants, inhibitors, hydrolysis stabilizers, light stabilizers, hindered amines light stabilizers, benzotriazole UV absorber, heat stabilizers, stabilizers to prevent discoloration, dyes, pigments, inorganic and organic fillers, reinforcing agents and combinations thereof.

All of the additives described above may be used in an effective amount customary for these substances. The non-flame retardants additives may be used in amounts of from about 0 to about 30 weight percent, in one embodiment from about 0.1 to about 25 weight percent, and in another embodiment about 0.1 to about 20 weight percent of the total weight of the TPU composition.

These additional additives can be incorporated into the components of, or into the reaction mixture for, the preparation of the TPU resin, or after making the TPU resin. In another process, all the materials can be mixed with the TPU resin and then melted or they can be incorporated directly into the melt of the TPU resin.

The thermoplastic polyurethanes of the invention can be prepared by processes which are conventional in the art for the synthesis of polyurethane elastomers such as but not limited to a batch process or a one-shot technique. In the batch process, the components, i.e., the diisocyanate(s), the polyol(s), and the chain extenders (s), as well as the catalyst(s) and any other additive(s), if desired, are introduced into a container, mixed, dispensed into trays and allowed to cure. The cured TPU can then be granulated and pelletized. The one-shot procedure is performed in an extruder, e.g. single screw, twin screw, wherein the formative components, introduced individually or as a mixture into the extruder, and reacted at a temperature generally in one embodiment from about 100° C. to about 300° C., and in another embodiment from about 150° C. to about 250° C., and even from about 150° C. to about 240° C.

One or more polymerization catalysts may be present during the polymerization reaction. Generally, any conventional catalyst can be utilized to react the diisocyanate with the polyol intermediates or the chain extender. Examples of suitable catalysts which in particular accelerate the reaction between the NCO groups of the diisocyanates and the hydroxy groups of the polyols and chain extenders are the conventional tertiary amines known from the prior art, e.g. triethylamine, dimethylcyclohexylamine, N-methylmorpholine, N,N'-dimethylpiperazine, 2-(dimethylaminoethoxy) ethanol, diazabicyclo[2.2.2]octane and the like, and also in particular organometallic compounds, such as titanic esters, iron compounds, e.g. ferric acetylacetonate, tin compounds, e.g. stannous diacetate, stannous dioctoate, stannous dilaurate, or the dialkyltin salts of aliphatic carboxylic acids, e.g. dibutyltin diacetate, dibutyltin dilaurate, or the like. The amounts usually used of the catalysts are from 0.0001 to 0.1 part by weight per 100 parts by weight of polyhydroxy compound (b).

The process may further include the step of: (II) mixing the TPU composition of step (I) with one or more blend components, including one or more additional TPU materials and/or polymers, including any of those described above.

The process may further include the step of: (II) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The process may further include the step of: (II) mixing the TPU composition of step (I) with one or more blend components, including one or more additional TPU materials and/or polymers, including any of those described above, and/or the step of: (III) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The Antimicrobial Additive

The antimicrobial additives for use in the disclosed technology provide antimicrobial properties to the compositions into which they are incorporated, and in some embodiments, they have at least two groups and/or reactive sites that can react with isocyanate groups to form covalent bonds. This is what allows them to react into the backbone of the base polymer described herein and what results in the described antimicrobial polymer compositions. In other embodiments, the antimicrobial additives are amenable to hydrogen bonding effects. This is what allows them to be chemically held in the compositions described herein and what results in the described antimicrobial polymer compositions.

Suitable antimicrobial additive includes deprotonated guanidine compounds, deprotonated biguanidine compounds, or a mixture thereof. These deprotonated compounds may be partially deprotonated guanidine and/or biguanidine compounds, fully deprotonated guanidine and/or biguanidine compounds, or mixtures thereof. In some embodiments, the antimicrobial additive is deprotonated polyhexamethylene biguanide (PHMB), also referred to as free base PHMB, and in some embodiments the antimicrobial additive is substantially free or even completely free of protonated PHMB. In other embodiments, the antimicrobial additive includes protonated PHMB. In some of these embodiments the antimicrobial additive is substantially free or even completely free of deprotonated PHMB.

In addition to the antimicrobial additive described above, one or more additional antimicrobial additives may be used in the compositions described herein. These additives would not react into the backbone in the way that those additives described will, but the additional antimicrobial additives could be added to the compositions in more convention ways, including (i) adsorption of the antimicrobial additive to the surface of materials passively or in combination with surfactants or by way of surface-bonded polymers; (ii) incorporation of the antimicrobial additive into a polymer coating applied on the material surface; (iii) compounding the antimicrobial additive into the bulk material comprising the device.

Suitable antimicrobial additives that may be used as these additional antimicrobial additives are not overly limited.

They can be organic or organometalic compounds such as quaternary ammonium salts, phenols, alcohols, aldehydes, iodophores, poly quats (such as oligermeric poly quats derivatized from an ethylenically unsaturated diamine and an ethylenically unsaturated dihalo compound), biguanides, benzoates, parabens, sorbates, propionates, imidazolidinyl urea, 1-(3-chloroallyl)-3,5,7-triaza-1-azoniaadamantane chloride (Dowacil 200, Quaternium), isothiazolones, DMDM hydantoin (2,3-imidazolidinedione), phenoxyethanol, bronopol, fluoroquinolones (such as ciprofloxacin), "potent" beta-lactams (third and fourth generation cephalosporins, carbapenems), beta-lactam/beta-lactamase inhibitors, glycopeptides, aminoglycosides, antibiotic drugs, heparin, phosphorylcholine compounds, sulfobetaine, carboxybetaine, and organometallic salts selected from silver salts, zinc salts, and copper salts and their derivatives. Examples of these antimicrobial agents includes pharmaceutical drugs such as penicillin, trichlosan, functional biguanides, mono-functional polyquaterniums, quaternized mono-functional polyvinylpyrrolidones (PVP), silane quaternary ammonium compounds, and other quaternized ammonium salts.

In one embodiment, the additional antimicrobial additive a quaternary ammonium molecule disclosed in U.S. Pat. No. 6,492,445 B2 (incorporated herein by reference).

Further examples of suitable mono-functional antimicrobial compounds include 2-hydroxyethyldimethyldodecyl ammonium chloride, 2-hydroxyethyldimethyloctadecylammonium chloride, esterquats such as Behenoyl PG-trimonium chloride from Mason Chemical Company, Fluoroquats. Other small molecular diol bearing antimicrobial active centers can be incorporated into polyurethane backbone as chain extender. Examples of such antimicrobial chain extender includes: diester quats such as Methyl bis[ethyl(tallowate)]-2-hydroxyethyl]ammonium methylsulfate (CAS No. 91995-81-2), Ethoquads such as Octadecylmethylbis(2-hydroxyethyl)ammonium chloride (CAS No. 3010-24-0), Oleyl-bis-(2-hydroxyethyl)methylammonium chloride, Polyoxyethylene(15)cocoalkylmethylammonium chloride (CAS No. 61791-10-4) available from Lion Akzo Co. Ltd, and the like.

However, in some embodiments no additional antimicrobial additives are present. Rather only the antimicrobial additives described above, which have at least two groups and/or reactive sites that can react with isocyanate groups to form covalent bonds, or which are extensively hydrogen-bonded to base polymer molecules, are used in the processes described herein and to make the compositions described herein. In other words, in some embodiments the antimicrobial additive is free of additives that do not have at least two groups and/or reactive sites that can react with isocyanate groups to form covalent bonds.

The antimicrobial additive may be present in the compositions described herein in any effective amount, that is, an amount that provides good antimicrobial performance. In some embodiments, good antimicrobial performance means a passing result in one or more of the tests described herein. In some embodiments, the antimicrobial additive is present in the described compositions from 0.1 to 10 percent by weight of the overall composition, or from 0.1 to 5, or from 0.1 to 4 percent by weight. In other embodiments, the antimicrobial additive is present in the described compositions from a lower limit of 0.1, 0.5, or 1.0 to an upper limit of 2.0, 4.0, 5.0, or 10 percent by weight. In some embodiments, the antimicrobial additive is present in the described compositions from 1.0 to 6.0 percent by weight. In still other embodiments, the antimicrobial additive is present in the described compositions from a lower limit of 1.5 or 2.0 to an upper limit of 3.0 or 3.5 percent by weight, or even 2.5 percent by weight.

The Surface-Modified Polymer Compositions

The surface-modified polymer compositions may be prepared by melt processing of the additive into the polymer, incorporation of the additive during polymer synthesis, casting or spinning a solvent mixture containing the additive and the polymer, or coating of the additive onto the base polymer from a solvent mixture containing the additive and the polymer.

In some embodiments, where the base polymer is a TPU, the diisocyanate, polyols and chain extender are mixed together either with or without catalysts, depending on the type of TPU being used. During the reaction, the polymeric or oligomeric surface modifying additives are preheated at 100° C. are poured into the reaction mixture. The resulting surface-modified TPU polymer can then be cut into cookies and granulated for extrusion or compression molding processes.

The surface modified polymer compositions may be prepared by melt mixing of the oligomeric or polymeric additives using a using a Brabender Plasticorder with the mixing bowl attachment. In some embodiments, the blends are run with the additives and the TPU are mixed as a mixture of solids (salt and pepper) prior to melt mixing. In some embodiments, the additive may be added to the base polymer following the initial charge of the base TPU had melted and the torque had stabilized. Alternatively, a twin screw extruder can be used to melt mix the additive into the TPU via typical methods know to those skilled in the art.

The polymer materials and/or compositions described herein may be used in the preparation of one or more articles. The specific type of articles that may be made from the polymer materials and/or compositions described herein are not overly limited. In general, the polymer materials and/or compositions described herein may be used in any application where a non-fouling or non-thrombogenic surface is desired.

The invention further provides an article made with the surface-modified polymer materials and/or compositions described herein. In some embodiments, the article may include a medical device. Examples include but are not limited to medical applications, for example, where the polymer described herein may be used in PICC, CVC, angioplasty, angioplasty and urology catheters, catheter connectors, medical tubing, and the like, as well as used in, personal care applications, pharmaceutical applications, health care product applications, marine applications, or any other number of applications. In some embodiments, these articles are prepared by extruding, injection molding, or any combination thereof.

The article made with the surface-modified polymer materials and/or compositions described herein may undergo further processing following formation. In one embodiment, further processing includes annealing. In one embodiment, annealing may be accomplished in an oven at temperature of from about 50° C. up to about 150° C. In some embodiments, annealing can occur for periods of from about two hours up to about seventy-two hours. In one embodiment, the annealing period may be for a period of at least 2 hours, or at least 12 hours, or at least 48 hours.

In some embodiments, a material used to form the article may be coated with the surface-modified polymer composition. The method of application of the coating is not overly limited, and can include dip coating, spray coating, roll-to-roll coating or spin coating. The coating may be applied at a thickness of from about 1 to several microns, or from about 2 to about 200. In other embodiments from 100 nm to 1 mm or from 1 um to 100 um. In some embodiments, following coating of the material used to form the medical device, the further step of annealing may be performed, as described above.

The surface modified polymer compositions as described herein can provide non-fouling and/or non-thrombogenic properties to the article prepared with the composition. In some embodiments, the polymer composition provides a reduction in protein absorption of at least 50 percent, or at least 60 percent, or 70 percent.

In some embodiments the disclosed technology provides a non-eluding antimicrobial polymer composition based on a zero zone of inhibition result when tested in the AATCC 147 assay when the antimicrobial additive has two or more of the described reactive groups capable of reacting with isocyanate groups and the mixing of the base polymer and the antimicrobial additive and the oligomeric or polymeric additive is done under controlled conditions that result in a small number of the urethane linkages in the polymeric backbone of the base polymer to reverse, or dissociate, and the relatively small number of broken polymer chains that now have reactive isocyanate groups react with the antimicrobial additive such that new polymers are formed where the broken polymer backbones reform with the antimicrobial additive present in the new backbone. Thus, the antimicrobial additive is not present as a pendant group connected to or bonded to the polymeric backbone. Further the antimicrobial additive is not present as a terminal group connected to or bonded to end of the polymeric backbone of the base polymer. Rather the antimicrobial additive of the disclosed technology is bonded into the backbone of the base polymer itself. Still further, the benefits of the disclosed technology cannot be achieved if the antimicrobial additive is added during the synthesis of the polymeric material, as the antimicrobial additive would not be properly disbursed throughout the backbones of the resulting base polymer. Also, since most antimicrobial additives have more than two reactive sites, they would act as cross linkers, forming an unusable highly crosslinked base polymer unsuitable for the uses and applications described herein if they were to be added during the synthesis of the TPU when reactive urethane group are abundant rather than during the extrusion when the number of isocyanate groups is significantly more limited. Finally, simply adding the antimicrobial additive to the base polymer under conditions that do not create the backbone breaking and reforming described here would not result in base compositions with the antimicrobial additives bonded into the backbone, but rather only simple mixtures where the antimicrobial additives is not bond to the polymeric material and where leaching would occur.

The non-leaching antimicrobial polymeric compositions of the disclosed technology, where the antimicrobial additives are bonded into the backbone of the base polymer, are achieved by careful control of the conditions under which the base polymer and antimicrobial additive are mixed.

It is further noted that the oligomeric or polymeric additive may be added to the base polymer at the same time the antimicrobial additive is added to the base polymer, or before the antimicrobial additive is added to the base polymer, or after the antimicrobial additive is added to the base polymer.

First, the thermoplastic polyurethanes of the invention can be prepared by processes which are conventional in the art for the synthesis of polyurethane elastomers such as but not limited to a two-step, batch process or a one-shot technique. In a two-step process, a polymer intermediate is reacted with an excess amount of diisocyanate, followed by chain extending the formed prepolymer. In the batch process, the components, i.e., the diisocyanate(s), the polyol(s), and the chain extenders (s), as well as the catalyst(s) and any other additive(s), if desired, are introduced into a reactor. After the initial reaction exotherm takes place the polymer melt is placed in an oven at 125-150 C for subsequent curing. The cured TPU can then be granulated and pelletized. The one-shot procedure is performed in an extruder, typically a twin screw extruder, wherein the formative components, are introduced individually or as a mixture into an extruder.

One or more polymerization catalysts may be present during the polymerization reaction. Generally, any conventional catalyst can be utilized to react the diisocyanate with the polyol intermediates or the chain extender. Examples of suitable catalysts which in particular accelerate the reaction between the NCO groups of the diisocyanates and the hydroxy groups of the polyols and chain extenders are the conventional tertiary amines known from the prior art, e.g. triethylamine, dimethylcyclohexylamine, N-methylmorpholine, N,N'-dimethylpiperazine, 2-(dimethylaminoethoxy) ethanol, diazabicyclo[2.2.2]octane and the like, and also in particular organometallic compounds, such as titanic esters, iron compounds, e.g. ferric acetyl acetonate, tin compounds, e.g. stannous diacetate, stannous dioctoate, stannous dilaurate, or the dialkyltin salts of aliphatic carboxylic acids, e.g. dibutyltin diacetate, dibutyltin dilaurate, or the like. The amounts usually used of the catalysts are from 0.0001 to 0.1 part by weight per 100 parts by weight of polyhydroxy compound (b).

The TPU materials described above may be prepared by a process that includes the step of: (I) reacting: a) the polyisocyanate component described above, that includes at least one aliphatic diisocyanate; b) the polyol component described above, that includes at least one polyester polyol; and c) the chain extender component described above that includes a substituted 2,5-diketopiperazine, as described above.

The process may further include the step of: (II) mixing the TPU composition of step (I) with one or more blend components, including one or more additional TPU materials and/or polymers, including any of those described above.

The process may further include the step of: (II) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, impact strength modifiers, and antimicrobials.

The process may further include the step of: (II) mixing the TPU composition of step (I) with one or more blend components, including one or more additional TPU materials and/or polymers, including any of those described above, and/or the step of: (III) mixing the TPU composition of step (I) with one or more additional additives selected from the group consisting of pigments, UV stabilizers, UV absorbers, antioxidants, lubricity agents, heat stabilizers, hydrolysis stabilizers, cross-linking activators, flame retardants, layered silicates, fillers, colorants, reinforcing agents, adhesion mediators, radio-opacifiers (such as BaSO4) impact strength modifiers, and antimicrobials.

The process may further include in step I of including a co-extender component that includes at least one diol chain extender of the general formula HO—$(CH_2)_x$—OH wherein x is an integer from 2 to 6.

Once the TPU is ready, it can be used as the base (?) polymeric material of the disclosed process and it can be mixed with the antimicrobial additive described above.

The carefully controlled mixing conditions must effectively melt the polymeric material, effectively mix the antimicrobial additive into the polymeric material, and also effectively reverse, or dissociate, a small number of urethane bonds in the backbone of the polymeric material.

In some embodiments, while not wishing to be bound by theory, applicants believe there is a dissociating a small number of urethane bonds in the backbone of the polymeric material. By this we mean, in some embodiments, less than 20% of all the bonds in the backbone of the polymeric material, or less than 10%, or less than 5% or less than 2%. In other embodiments, it means from 0.1 to 20% of the bonds, or from 0.1 to 10, 0.1 to 5, 0.1 to 2% of the urethane bonds. In other embodiments, it means from 1 to 20% of the bonds, or from 1 to 10, 1 to 5, 1 to 2% of the urethane bonds. In still other embodiments it means from about 0.1, 0.2, 0.5, or 1% to 2, 3, or 5% of the urethane bonds. In some embodiments, dissociating a small number of urethane bonds in the backbone of the polymeric material means from 0.1% to 2% or form 0.1 to 5% of all the urethane bonds in the backbone of the polymeric material. For additional information on urethane bond breaking, see Chemical Review, 2013, 113 (1), pp 80-118 and Macromolecular Materials and Engineering, 2003, 288 (6), pp 525-530, which are both incorporated by reference.

The disclosed technology further discloses the described process where the mixing occurs in a mixing device at a temperature from 160 to 225 degrees Celsius. The mixing may also occur from 180 to 225, or from 160 to 200 degrees Celsius.

In some embodiments, where the polymeric materials includes an aliphatic TPU (a TPU made from an aliphatic diisocyanate), the mixing occurs in a mixing device at a temperature from 160 to 200 degrees Celsius. The mixing may also occur from 155 to 175, or from 160 to 180, or even from 165 to 185 degrees Celsius.

In some embodiments, where the polymeric materials includes an aromatic TPU (a TPU made from an aromatic diisocyanate), the mixing occurs in a mixing device at a temperature from 180 to 220 degrees Celsius. The mixing may also occur from 175 to 215, or from 180 to 220, or even from 185 to 225 degrees Celsius.

The disclosed technology further discloses the described process where the mixing occurs in an extruder where the antimicrobial additive and the oligomeric or polymeric additive are added to the polymeric material and wherein said mixing occurs at a temperature between 180 and 225 degrees Celsius, where the extruder comprises a twin screw extruder with co-rotating, self-wiping screws, with a mixture of conveying and mixing elements, and a length to diameter ratio of 20:1 to 50:1, or from 30:1 to 50:1. In other embodiments the described process in the described extruder occurs at 160 to 200, 155 to 175, 160 to 180, or 165 to 185 degrees Celsius. In other embodiments, the described process in the described extruder occurs at 180 to 220, 175 to 215, 180 to 220, or 185 to 225 degrees Celsius.

The amount of each chemical component described is presented exclusive of any solvent which may be customarily present in the commercial material, that is, on an active chemical basis, unless otherwise indicated. However, unless otherwise indicated, each chemical or composition referred to herein should be interpreted as being a commercial grade material which may contain the isomers, by-products, derivatives, and other such materials which are normally understood to be present in the commercial grade.

Antimicrobial Properties

Persons skilled in the art are well aware of what is meant by the term "antimicrobial." Moreover, persons skilled in the art are familiar with a wide variety of chemical substances that have antimicrobial properties. Nevertheless, Applicants provide a quantitative definition of the term "antimicrobial" in the context of the present invention. An antimicrobial additive of the present invention is an additive which imparts to the polymer containing it the ability to reduce the concentration of *E. coli* at the surface of the polymer by a factor of 50% with reference to the effect of an otherwise similar polymer In other embodiments, the TPU materials and/or compositions described herein may be used as medical devices, such as implants or coatings on implants, where the TPU delivers one or more therapeutic agents at the site of implantation. The terms "therapeutic agents" and "drugs" are used herein interchangeably to mean any material that has a therapeutic effect at an implantation site. Also, as used herein, the device of the present invention is said to "deliver" or "elute" therapeutic agent—these terms are used synonymously and generally to refer to any mechanism by which the therapeutic agent migrates form the polymer to the biologic tissue and in doing so provides therapeutic effects.

The therapeutic agent(s) may be delivered in a number of ways. In one example, the therapeutic agent(s) are embedded within a coating that is made using the TPU materials and/or compositions described herein that adheres to one or more surfaces of an implant or other medical article or medical device. In some embodiments, the coating is made from one or more of the TPU materials and/or compositions described herein admixed with the therapeutic agent(s) such that the agent is eluted from the polymer over time, or is released from the coating as it degrades in-vivo. In some embodiments one or more therapeutic agents are applied in discrete areas on one or more individual section or surfaces of the implant or other medical article or medical device.

The Articles

The compositions described herein may be used in the preparation of one or more articles. The specific type of articles that may be made from the TPU materials and/or compositions described herein are not overly limited.

The invention further provides an article made with the TPU materials and/or compositions described herein. Examples include but are not limited to medical applications, as well as used in, personal care applications, pharmaceutical applications, health care product applications, or any other number of applications. In some embodiments, these articles are prepared by extruding, injection molding, compression molding, spinning or casting films or fibers, or any combination thereof.

In some embodiments, the compositions described herein are used to make tubular medical devices. Tubular medical articles within the meaning of the present invention are those medical articles that can conduct fluids. In particular, the medical articles are selected from the group consisting of catheters, central venous catheters, peripheral venous catheters, breathing tubes, stents, couplings, ports, conduit systems, connectors, spikes, valves, three-way stopcocks, syringes, conduits, injection ports, wound drains, thoracic drains and probes.

Other suitable medical articles that can be made using the compositions of described here include central venous catheters; peripheral venous catheters; breathing tubes, stents; products for application in regional anesthesia, especially catheters, couplings, filters; products for infusion therapy, especially containers, ports, conduit systems, filters; accessories, such as connectors, spikes, valves, three-way stopcocks, syringes, conduits, injection ports; products of formulation, especially transfer sets, mixing sets; dialysis membranes; urological products, especially catheters, urine measuring and collecting devices; wound drains; wound dressing; surgical suture materials; implantation auxiliaries as well as implants, especially plastic implants, for example, hernia meshes, non-wovens, knitwear/knitted fabrics, ports, port catheters, vascular prostheses; disinfectants; disposable surgical instruments; thoracic drains; probes; catheters; housings of medical devices, especially infusion pumps, dialysis devices and screens; artificial dentures; containers for liquids, especially contact lens containers.

In some embodiments, the compositions described herein are used to make PICC catheters and CVC catheters.

It is known that some of the materials described above may interact in the final formulation, so that the components of the final formulation may be different from those that are initially added. For instance, metal ions (of, e.g., a flame retardant) can migrate to other acidic or anionic sites of other molecules. The products formed thereby, including the products formed upon employing the composition of the technology described herein in its intended use, may not be susceptible of easy description. Nevertheless, all such modifications and reaction products are included within the scope of the technology described herein; the technology described herein encompasses the composition prepared by admixing the components described above.

EXAMPLES

The technology described herein may be better understood with reference to the following non-limiting examples.

The examples provided below are evaluated to determine their antimicrobial performance by various tests including JIS Z2801 and the Innovotech Best Assay, and to test their non-thrombogenic properties via the Throbodyne bovine blood loop assay.

Materials:

The following materials were used in the preparation of Examples 1 to 3:

(1) free base PHMB, a free base (deprotonated) PHMB obtained from Matrix.

(2) neutral PHMB, a neutral pH protonated PHMB obtained from Lonza.

(3) TPU A, Tecothane™ TT1095A, and aromatic polyether TPU of 93 Shore A hardness commercially available from Lubrizol.
(4) TPU B, Tecoflex™ EG93A-B30, an aliphatic polyether TPU of 90 Shore A hardness commercially available from Lubrizol, modified with a radiopacifier.
(5) PEGFOM, a random copolymer of polyethylene glycol methacrylate, Capstone 62MA, and methyl methacrylate, which is further described in WO 2016/172460.

Preparation of antimicrobial polymeric compositions: For each example an antimicrobial additive PHMB and a TPU is fed with gravimetric feeders into a 26 mm twin screw extruder with co-rotating, self-wiping screws with both conveying and mixing elements and a L/D ratio of 39:1. The strands are extruded into a chilled water bath and cut into pellets. Pellets are later compression molded into films or extruded into tubing for additional testing. Additive loading level was confirmed by NMR and in all cases was essentially equal to the ratio of additives fed into the extruder. Formulations and performance results are summarized in Table 1.

The Examples shown below are tested for antimicrobial efficacy by the standard test method JIS Z2801 and also by the Innovotech BEST™ assay.[5] Results of antimicrobial efficacy testing on various compositions are indicated in Tablet.

The example shown below are also evaluated for their antimicrobial and non-thrombogenic properties. The examples were extruded into tubing (60 thousandths of an inch outer diameter), annealed for two days at 50° C. were tested in the bovine blood loop assay at Thrombodyne in Salt Lake City, Utah. The procedure for this assay involves exposing the tubes in a bovine blood flow loop. The results reported for the blood loop assay test are the percent control of thrombosis that is the relative amount of thrombosis accumulation, the sample experiences relative to the baseline TPU, which is reported at 100%. Thus, a lower value indicated better non-fouling performance.

For more information on the Innovotech BEST' assay see Omar, A., Nadworny, P., Review: Antimicrobial efficacy validation using in vitro and in vivo testing methods. *Advanced Drug Delivery Reviews*, In Press, incorporated herein by reference. For more information on the bovine blood loop assay see Zhang, Z.; Borenstein, J.; Guiney, L.; Miller, R.; Sukavaneshvar, S.; Loose, C., Polybetaine modification of PDMS microfluidic devices to resist thrombus formation in whole blood. *Lab on a Chip* 2013, 13 (10), 1963-1968 and Sukavaneshvar, S., Device thrombosis and pre-clinical blood flow models for assessing antithrombogenic efficacy of drug-device combinations. *Advanced Drug Delivery Reviews*, incorporated herein by reference.

The JIS Z 2801 method (adopted as an International Organization for Standardization procedure, ISO 22196) tests the ability of materials including plastics, to inhibit the growth of microorganisms or kill them. The procedure is very sensitive to antimicrobial activity and has become the most common test for antimicrobial hard surface performance in the United States. The JIS Z 2801 test method is designed to quantitatively test the ability of hard surfaces to inhibit the growth of microorganisms or kill them, over a 24 hour period of contact. In the JIS Z 2801 Test: (i) the test microorganism is prepared, (ii) the suspension of test microorganism is standardized by dilution in a nutritive broth, (iii) control and test surfaces are inoculated with microorganisms and the microbial inoculum is covered with a thin, sterile film, (iv) microbial concentrations are determined at "time zero" by elution followed by dilution and plating, (v) a control is run with the samples, (vi) samples are incubated undisturbed in a humid environment for 24 hours, (vii) after incubation, microbial concentrations are determined. The reduction of microorganisms relative to initial concentrations and the control surface is calculated, thus higher results indicate better antimicrobial performance.

TABLE 1

| Formulation | JIS Z2801 S. aureus (log. Red.) | JIS Z2801 E. coli (log. Red.) | BEST™ S. aureus (log. Red.) | BEST™ E. coli (log. Red.) | Blood Loop Assay % Control - Relative Thrombosis Accumulation |
|---|---|---|---|---|---|
| Example 1 TT1095A | n/a | n/a | n/a | n/a | 100 |
| Example 2 1% Matrix PHMB in TPU A | >4.8 | 2.3 | n/a | n/a | 101 |
| Example 3 1% Matrix PHMB 5% PEGFOM in TPU A | >5.3 | >1.8 | n/a | n/a | 16.5 |
| Example 4 EG93A | n/a | n/a | n/a | n/a | 100 |
| Example 5 4% Lonza PHMB in TPU B | >5.20 | >5.05 | 4.5 | 3.1 | n/a |
| Example 6 1% Lonza PHMB 3% PEGFOM in TPU B | >5.20 | >5.05 | n/a | n/a | n/a |
| Example 7 2% Lonza PHMB 3% PEGFOM in TPU B | >5.20 | >5.05 | n/a | n/a | n/a |
| Example 8 4% Lonza PHMB 9% PEGFOM in TPU B | n/a | n/a | 5.4 | 5.8 | 8 |

The results show that when PHMB (in either a deprotonated or deprotonated form) is used, antimicrobial performance is significantly improved compared to the TPU itself. Further the results show that when PHMB is used in combination with PEGFOM, the resulting TPU composition has good antimicrobial and good non-fouling performance, that is, the additives do not interfere with one another and are able to provide both benefits in the resulting composition.

Table 2 shows additional examples which may be tested for their antimicrobial performance, where different forms and amounts of PHMB are used:

TABLE 2

| Example | TPU | % Matrix PHMB | % Lonza PHMB | % PEGFOM | Example | TPU | % Matrix PHMB | % Lonza PHMB | % PEGFOM |
|---|---|---|---|---|---|---|---|---|---|
| 2-1 | A | 0% | 0% | 0% | 2-11 | B | 0% | 0% | 0% |
| 2-2 | A | 1% | 0% | 0% | 2-12 | B | 1% | 0% | 0% |
| 2-3 | A | 0% | 1% | 0% | 2-13 | B | 0% | 1% | 0% |
| 2-4 | A | 0% | 0% | 4% | 2-14 | B | 0% | 0% | 4% |
| 2-5 | A | 1% | 1% | 0% | 2-15 | B | 1% | 1% | 0% |
| 2-6 | A | 0% | 1% | 4% | 2-16 | B | 0% | 1% | 4% |
| 2-7 | A | 1% | 0% | 4% | 2-17 | B | 1% | 0% | 4% |
| 2-8 | A | 2% | 0% | 4% | 2-18 | B | 2% | 0% | 4% |
| 2-9 | A | 0% | 2% | 4% | 2-19 | B | 0% | 2% | 4% |
| 2-10 | A | 2% | 2% | 4% | 2-20 | B | 2% | 2% | 4% |

Each of the documents referred to above is incorporated herein by reference, including any prior applications, whether or not specifically listed above, from which priority is claimed. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about." It is to be understood that the upper and lower amount, range, and ratio limits set forth herein may be independently combined. Similarly, the ranges and amounts for each element of the technology described herein can be used together with ranges or amounts for any of the other elements.

As described hereinafter the molecular weight of the materials described above have been determined using known methods, such as GPC analysis using polystyrene standards. Methods for determining molecular weights of polymers are well known. The methods are described for instance: (i) P. J. Flory, "Principles of star polymer Chemistry", Cornell University Press 91953), Chapter VII, pp 266-315; or (ii) "Macromolecules, an Introduction to star polymer Science", F. A. Bovey and F. H. Winslow, Editors, Academic Press (1979), pp 296-312. As used herein the weight average and number weight average molecular weights of the materials described are obtained by integrating the area under the peak corresponding to the material of interest, excluding peaks associated with diluents, impurities, uncoupled star polymer chains and other additives.

As used herein, the transitional term "comprising," which is synonymous with "including," "containing," or "characterized by," is inclusive or open-ended and does not exclude additional, un-recited elements or method steps. However, in each recitation of "comprising" herein, it is intended that the term also encompass, as alternative embodiments, the phrases "consisting essentially of" and "consisting of," where "consisting of" excludes any element or step not specified and "consisting essentially of" permits the inclusion of additional un-recited elements or steps that do not materially affect the basic and novel characteristics of the composition or method under consideration. That is "consisting essentially of" permits the inclusion of substances that do not materially affect the basic and novel characteristics of the composition under consideration.

While certain representative embodiments and details have been shown for the purpose of illustrating the subject technology described herein, it will be apparent to those skilled in this art that various changes and modifications can be made therein without departing from the scope of the subject invention. In this regard, the scope of the technology described herein is to be limited only by the following claims.

What is claimed is:

1. A surface modifying polymer composition comprising:
   a) a polymeric additive formed from:
      i) a polyalkylene glycol monomer;
      ii) a fluorocarbon monomer represented by the formula D-E-F, wherein D is a polymerizable group selected from acrylate, methacrylate, vinyl, or an active hydrogen group selected from an alcohol, amine or thiol, E is an optional linking group, and F is fluorocarbon group; and
      iii) an alkyl substituted methacrylate, acrylate, acrylamide, or vinyl monomer, or combinations thereof;
   b) a base polymer comprising a thermoplastic polyurethane polymer backbone; and
   c) an antimicrobial additive comprising a protonated guanidine compound, a protonated biguanidine compound, or a mixture thereof;
   wherein component (a) and component (c) are incorporated into the base polymer by melt processing wherein some portion of said protonated guanidine compound, said protonated biguanidine compound, or said mixture of protonated guanidine compound and protonated biguanidine compound is hydrogen bonded to the polymeric backbone of said base polymer.

2. The composition of claim 1, wherein said protonated biguanidine compound comprises protonated polyhexamethylene biguanidine.

3. The composition of claim 1 wherein the thermoplastic polyurethane is derived from (a) diphenylmethane diisocyanate, (b) a polyether polyol, and (c) a butane diol chain extender component.

* * * * *